US009149572B2

(12) United States Patent
Kojima et al.

(10) Patent No.: US 9,149,572 B2
(45) Date of Patent: Oct. 6, 2015

(54) CHONDROITIN SULFATE HAVING DECREASED MOLECULAR WEIGHT AND USE THEREOF

(71) Applicant: Seikagaku Corporation, Tokyo (JP)

(72) Inventors: Kazuhiro Kojima, Tokyo (JP); Yukio Goto, Tokyo (JP); Hiroshi Maeda, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 51 days.

(21) Appl. No.: 13/782,165

(22) Filed: Mar. 1, 2013

(65) Prior Publication Data

US 2013/0196943 A1   Aug. 1, 2013

Related U.S. Application Data

(62) Division of application No. 12/680,995, filed as application No. PCT/JP2008/067805 on Oct. 1, 2008, now abandoned.

(30) Foreign Application Priority Data

Oct. 1, 2007   (JP) .................................. 2007-257945
Apr. 18, 2008  (JP) .................................. 2008-109492

(51) Int. Cl.
   *A61M 1/28*      (2006.01)
   *A61K 31/726*    (2006.01)
   *A61K 31/737*    (2006.01)
   *C08B 37/00*     (2006.01)
   *C08J 3/28*      (2006.01)
   *C08L 5/08*      (2006.01)

(52) U.S. Cl.
   CPC .............. *A61M 1/287* (2013.01); *A61K 31/726* (2013.01); *A61K 31/737* (2013.01); *C08B 37/0069* (2013.01); *C08J 3/28* (2013.01); *C08L 5/08* (2013.01); *C08J 2305/08* (2013.01)

(58) Field of Classification Search
   None
   See application file for complete search history.

(56) References Cited

FOREIGN PATENT DOCUMENTS

| EP | 0 710 483 A1 | 5/1996 |
|---|---|---|
| JP | 57-040502 | 3/1982 |
| JP | 1-151462 | 6/1989 |
| JP | 5-345021 | 12/1993 |
| JP | 2004-43645 | 2/2004 |
| JP | 2004-217594 | 8/2004 |
| WO | WO 93/14796 | 8/1993 |
| WO | 93/21193 | 10/1993 |
| WO | WO 98/01141 | 1/1998 |
| WO | WO 2006/068146 A1 | 6/2006 |

OTHER PUBLICATIONS

International Search Report regarding Application No. PCT/JP2008/067805 mailed Dec. 22, 2008.
Supplemental European Search Report regarding Application No. 08836443.5-2123 dated Jul. 22, 2011.
Imada, A. et al.: "The Usefulness of Chondroitin Sulfate as an Osmotic Agent for Peritoneal Dialysis", Nephrology Dialysis Transplantation, Oxford University Press, GB, vol. 11, No. 6, Jun. 1, 1996, p. A246, XP002043772, ISSN: 0931-0509 *abstract*.
Struijk, Dirk G., et al.: "Future Research in Peritoneal Dialysis Fluids", Seminars in Dialysis, vol. 11, No. 4, Jul. 1, 1998, pp. 207-212, XP55002691, ISSN: 0894-0959.
Campo, G. M., et al.: "Chondroitin sulphate: antioxidant properties and beneficial effects.", Mini Reviews in Medicinal Chemistry Dec. 2006 LNKDPUBMED: 17168807, vol. 6, No. 12, pp. 1311-1320, XP009150269, ISSN: 1389-7757.
Japanese Office Action dated May 21, 2013, in the corresponding Japanese patent application No. 2009-536064.

*Primary Examiner* — Eric Olson
*Assistant Examiner* — Dale R Miller
(74) *Attorney, Agent, or Firm* — Kratz, Quintos & Hanson, LLP

(57) ABSTRACT

A chondroitin sulfate having a decreased molecular weight which has utilization as an inhibitor of peritoneal disorder caused by long-term use of a peritoneal dialysis fluid containing glucose or a polysaccharide thereof as an osmotic agent, utilization as an osmotic agent in a peritoneal dialysis fluid, and the like. The chondroitin sulfate having a decreased molecular weight of the present invention as a means for achieving the object is characterized by having a weight average molecular weight of from 1000 to 20000 and containing a constituent disaccharide unit represented by the following structural formula in an amount of from 65% to 100% (molar ratio) of the total:

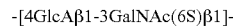

(wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated).

4 Claims, 2 Drawing Sheets

CHONDROITIN SULFATE HAVING DECREASED MOLECULAR WEIGHT AND USE THEREOF

CROSS-REFERENCE TO RELATED APPLICATIONS

This Application is a divisional of U.S. application Ser. No. 12/680,995, with 371(c) date of Jun. 9, 2010, which is a 371 National stage application of PCT/JP2008/067805, filed on Oct. 1, 2008, which is hereby incorporated by reference.

TECHNICAL FIELD

The present invention relates to a novel chondroitin sulfate having a decreased molecular weight and use thereof. More particularly, the present invention relates to a chondroitin sulfate having a decreased molecular weight which has utilization as an inhibitor of peritoneal disorder caused by long-term use of a peritoneal dialysis fluid containing glucose or a polysaccharide thereof as an osmotic agent, utilization as an osmotic agent in a peritoneal dialysis fluid, and the like, and use thereof.

BACKGROUND ART

Artificial dialysis for patients with end-stage renal failure is broadly divided into hemodialysis and peritoneal dialysis. Among these, the peritoneal dialysis is a method in which a hypertonic dialysis fluid containing glucose or a polysaccharide thereof as an osmotic agent is injected into the peritoneal cavity and excess waste products, water, and electrolytes in the body are removed with the use of the function of the peritoneum as a semipermeable membrane. The peritoneal dialysis has many advantages as compared with the hemodialysis in that the need for dietary or activity restriction is lower, the effect on hemodynamics is lower, preservation of residual renal function is better, rehabilitation is easier, etc. However, in recent years, various disorders due to prolonged peritoneal dialysis, for example, poor water removal or insufficient removal of waste products accompanying deterioration of peritoneal function has become a serious problem. The deterioration of peritoneal function is deeply associated with an advanced glycation end product (AGE) generated by a reaction between glucose contained in a peritoneal dialysis fluid as an osmotic agent and a protein, a reactive oxygen species (ROS) produced by binding of AGE to a cell having a receptor thereof or exposure of the cell to high concentration of glucose.

In order to solve the problems as described above, a search for a substance that inhibits deterioration of peritoneal function caused by glucose or a polysaccharide thereof and a search for a novel osmotic agent alternative to glucose or a polysaccharide thereof have been performed, and a chondroitin sulfate (CS) which is a sulfated glycosaminoglycan has already been proposed as a candidate substance (For example, Patent Document 1 and Non-patent Document 1).
Patent Document 1: JP-A-1-151462
Non-patent Document 1: Ohno T., Imada A., "The usefulness of sodium chondroitin sulfate as an osmotic agent for peritoneal dialysis", Toseki kaishi (The Journal of the Japanese Society for Dialysis Therapy), 30(1): 65, 1997

DISCLOSURE OF THE INVENTION

Problems that the Invention is to Solve

A chondroitin sulfate is a substance in the body and therefore has high biocompatibility and little effect on the blood coagulation system unlike heparin. Accordingly, a chondroitin sulfate is considered to be promising also from a safety standpoint. However, although it has been reported that in the evaluation using an animal model, a chondroitin sulfate has an action of protecting the peritoneal function (Non-patent Document 1), it has also been reported that a chondroitin sulfate does not have such a protective action (Suyama K., Kumano K., Sakai T., "Agents preventing decrease in ultrafiltration in a rat model with peritoneal hyperpermeability", Nippon Jinzo Gakkai Shi (The Japanese Journal of Nephrology), 37(9): 491, 1995). Thus, the current situation is that the views as to the usefulness of a chondroitin sulfate are still controversial. In addition, in the chondroitin sulfate, there are several types based on a difference in the binding site of a sulfate group such as chondroitin sulfate A, chondroitin sulfate C, chondroitin sulfate D, and chondroitin sulfate E, and also there is significant structural diversity. Therefore, it is considered that functional diversity may arise from the structural diversity, however, as far as the present inventors know, there has been no report that a relationship between the structure and the function of a chondroitin sulfate in peritoneal dialysis is elucidated.

Accordingly, an object of the present invention is to provide a novel chondroitin sulfate useful in peritoneal dialysis.

Means for Solving the Problems

In view of the above points, the present inventors conducted intensive studies, and as a result, they found that a chondroitin sulfate having a decreased molecular weight having a specific molecular weight and containing a specific constituent disaccharide unit in a specific percentage of the total is useful as an inhibitor of peritoneal disorder caused by long-term use of a peritoneal dialysis fluid containing glucose or a polysaccharide thereof as an osmotic agent, useful as an osmotic agent in a peritoneal dialysis fluid, and the like, based on excellent action of inhibiting AGE production and action of scavenging reactive oxygen.

In a fist embodiment, a chondroitin sulfate having a decreased molecular weight of the present invention completed based on the above findings is characterized by having a weight average molecular weight of from 1000 to 20000 and containing a constituent disaccharide unit represented by the following structural formula in an amount of from 65% to 100% (molar ratio) of the total.

-[4GlcAβ1-3GalNAc(6S)β1]-

(wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated)

Further, in a second embodiment, a peritoneal dialysis fluid of the present invention is characterized by containing the chondroitin sulfate having a decreased molecular weight according to the first embodiment.

Further, in a third embodiment, a compounding agent for a peritoneal dialysis fluid of the present invention is characterized by containing the chondroitin sulfate having a decreased molecular weight according to the first embodiment as an active ingredient.

Further, in a fourth embodiment, an inhibitor of peritoneal disorder caused by a peritoneal dialysis fluid containing glucose and/or a polysaccharide thereof as an osmotic agent of the present invention is characterized by containing the chondroitin sulfate having a decreased molecular weight according to the first embodiment as an active ingredient.

Further, in a fifth embodiment, an AGE production inhibitor of the present invention is characterized by containing the chondroitin sulfate having a decreased molecular weight according to the first embodiment as an active ingredient.

Further, in a sixth embodiment, a reactive oxygen scavenger of the present invention is characterized by containing the chondroitin sulfate having a decreased molecular weight according to the first embodiment as an active ingredient.

Further, in a seventh embodiment, an inhibitor of lipid peroxidation of the present invention is characterized by containing the chondroitin sulfate having a decreased molecular weight according to the first embodiment as an active ingredient.

Effect of the Invention

According to the present invention, a chondroitin sulfate having a decreased molecular weight which has utilization as an inhibitor of peritoneal disorder caused by long-term use of a peritoneal dialysis fluid containing glucose or a polysaccharide thereof as an osmotic agent, utilization as an osmotic agent in a peritoneal dialysis fluid, and the like can be provided.

BEST MODE FOR CARRYING OUT THE INVENTION

Figure 1:
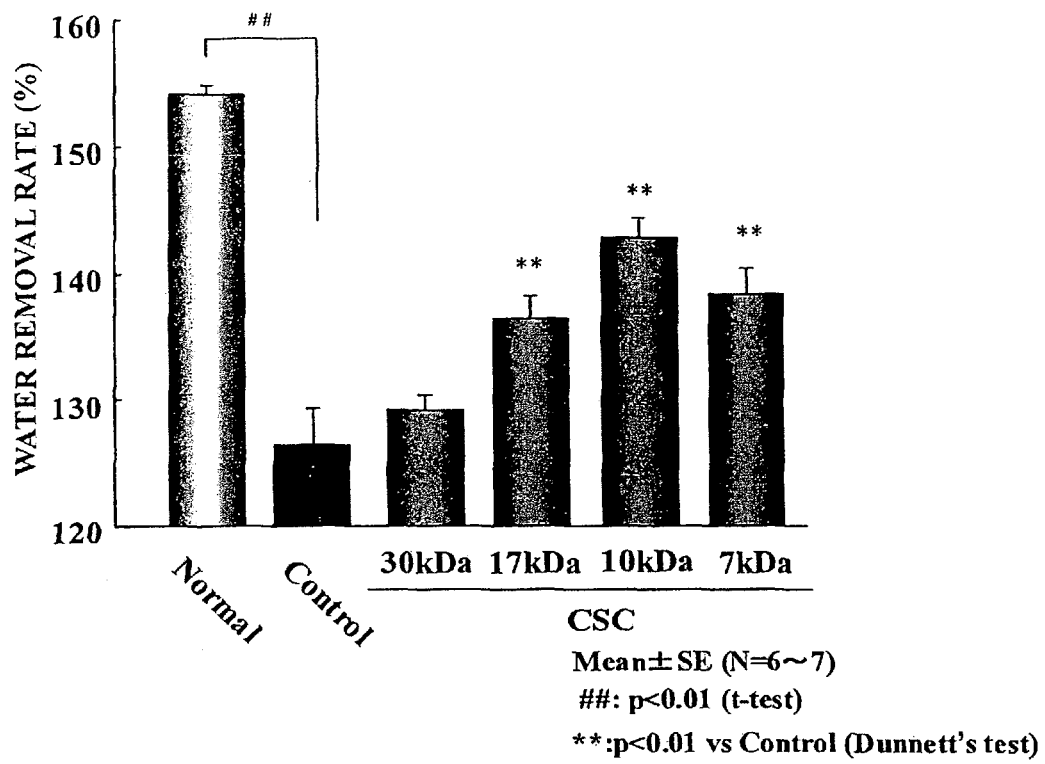
FIG. 1 A graph showing an effect of protecting the peritoneum (action of inhibiting a decrease in water removal rate) in peritoneal dialysis of a chondroitin sulfate having a decreased molecular weight of the present invention in Example 3.

The chondroitin sulfate having a decreased molecular weight of the present invention, which has utilization as an inhibitor of peritoneal disorder caused by long-term use of a peritoneal dialysis fluid containing glucose or a polysaccharide thereof as an osmotic agent, utilization as an osmotic agent in a peritoneal dialysis fluid, and the like, is characterized by having a weight average molecular weight of from 1000 to 20000 and containing a constituent disaccharide unit represented by the following structural formula in an amount of from 65% to 100% (molar ratio) of the total.

-[4GlcAβ1-3GalNAc(6S)β1]-

(wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated)

The chondroitin sulfate having a decreased molecular weight of the present invention can be prepared by, for example, using chondroitin sulfate C (chondroitin 6-sulfate) containing a constituent disaccharide unit represented by the following structural formula in an amount of from 65% to 100% (molar ratio) of the total as a starting material and reducing the molecular weight of the starting material such that the weight average molecular weight becomes 1000 to 20000, preferably 5000 to 18000. As the chondroitin sulfate C to be used as the starting material, for example, Prionace glauca-derived chondroitin sulfate C (trade name of Seikagaku Corporation: Chondroitin sulfate C, sodium salt (shark cartilage), SG) can be used. The reduction of the molecular weight thereof can be performed by a degradation method using electron beam irradiation described in JP-A-2004-43645 or the like as well as the methods such as a chemical degradation method using hydrochloric acid and an enzymatic degradation method using ovine testicular hyaluronidase which are known methods of reducing the molecular weight of a chondroitin sulfate. Incidentally, the content percentage of the constituent disaccharide unit represented by the following structural formula in the starting material is not necessarily 65% or more (molar ratio) of the total and may be less than 65% (molar ratio) as long as a fraction of 65% or more (molar ratio) can be obtained by fractional purification. Further, the chondroitin sulfate having a decreased molecular weight of the present invention may be a product obtained by chemical synthesis or extraction from a cultured product or a fermented product of a biological tissue of shark or the like.

-[4GlcAβ1-3GalNAc(6S)β1]-

(wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated)

The chondroitin sulfate having a decreased molecular weight of the present invention has excellent action of inhibiting AGE production and action of scavenging reactive oxygen. Therefore, by adding the chondroitin sulfate to a peritoneal dialysis fluid containing glucose or a polysaccharide thereof as an osmotic agent, an effect as an inhibitor of peritoneal disorder (e.g., lipid peroxidation) caused by glucose or a polysaccharide thereof due to long-term use of such a peritoneal dialysis fluid can be exhibited. Further, the chondroitin sulfate having a decreased molecular weight of the present invention can also be added to a peritoneal dialysis fluid as an osmotic agent in the peritoneal dialysis fluid.

In the case where the chondroitin sulfate having a decreased molecular weight of the present invention is added to a conventional peritoneal dialysis fluid containing glucose or a polysaccharide thereof as an osmotic agent, the chondroitin sulfate may be added at a concentration of from 0.01% (w/v) to 1% (w/v). Further, in the case where a peritoneal dialysis fluid is prepared by adding the chondroitin sulfate having a decreased molecular weight of the present invention as an osmotic agent alternative to glucose or a polysaccharide thereof, the chondroitin sulfate may be added at a concentration of from 1% (w/v) to 10% (w/v) to constitute the peritoneal dialysis fluid together with components known as constituent components of the peritoneal dialysis fluid such as sodium, magnesium, calcium, chlorine, and lactic acid.

Further, the action of inhibiting AGE production of the chondroitin sulfate having a decreased molecular weight of the present invention is effective in the treatment of diabetes, various diabetic complications (for example, diabetic retinopathy, diabetic nephropathy, diabetic neuropathy, and diabetic vascular complications), etc., and the action of scavenging reactive oxygen of it is effective in the treatment of cancer, cataract, arteriosclerosis, Alzheimer's disease, asthma, etc. Therefore, the chondroitin sulfate having a decreased molecular weight of the present invention can also be used as an active ingredient for treating such a disease. In this case, the chondroitin sulfate having a decreased molecular weight of the present invention may be administered orally or parenterally at a dose appropriately determined based on the degree of symptoms, age, and body weight of a patient or the like. It can be administered in a known dosage form.

EXAMPLES

Hereinafter, the present invention will be described in further detail with reference to Examples, however, the invention is not limited to the following description. Incidentally, in the Examples, the molecular weight is indicated in "kDa" (1 kDa=1000).

Example 1

Preparation of Chondroitin Sulfate Having Decreased Molecular Weight of the Present Invention (1)

Prionace glauca-derived chondroitin sulfate C (weight average molecular weight: 30 kDa, trade name of Seikagaku Corporation: Chondroitin sulfate C, sodium salt (shark cartilage), SG) was used as a starting material and dissolved in an amount of 1 g in 50 mL of PBS (pH 5.3). To this solution, 100,000 U of ovine testicular hyaluronidase (manufactured by Sigma, type V) was added, and the enzymatic reaction was allowed to proceed at 37° C. A portion of the reaction mixture was taken over time and analyzed by GPC-HPLC to examine the degree of reduction of the molecular weight. When a desired molecular weight was obtained, the reaction mixture was boiled to stop the enzymatic reaction. In the case where the desired molecular weight was not obtained, ovine testicular hyaluronidase was further added to the reaction mixture and the enzymatic reaction was allowed to proceed. When the desired molecular weight was obtained, the reaction mixture was boiled to stop the enzymatic reaction. After completion of the reaction, activated carbon was added to the thus obtained desired molecular weight fraction, and the reaction was allowed to proceed at 50° C. for 1 hour. Thereafter, the reaction mixture was filtered, and to the filtrate, sodium acetate trihydrate was added, and then, ethanol was added thereto to obtain precipitates. The obtained precipitates were purified by washing with ethanol and drying. By the above-mentioned method, a chondroitin sulfate having a decreased molecular weight of the present invention having a weight average molecular weight of 10 kDa and containing a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) in an amount of 74.0% (molar ratio) of the total was obtained as white powder (the detail of the composition of the constituent disaccharide is as shown in Table 1).

Incidentally, the analysis of the composition of the constituent disaccharide was performed as follows. 100 μL of a measurement sample (about 200 μg/mL) was taken, 40 μL of 100 mM Tris-HCl buffer (pH 8.0) and Chondroitinase ABC (83 mU, manufactured by Seikagaku Corporation) were added thereto, and the total volume was made up to 200 μL. The reaction was allowed to proceed at 37° C. for 3 hours, and the resulting reaction mixture was filtered through a 10000 cut-off ultrafilter, and the filtrate was subjected to HPLC (column: YMC gel PA-120, manufactured by YMC Co., Ltd.). (The same shall apply to Example 2)

TABLE 1

| | Disaccharide composition ratio (%) | | | | | |
|---|---|---|---|---|---|---|
| | 0S | 6S | 4S | SD | SB | SE |
| CSC 10 kDa | 1.0 | 74.0 | 14.0 | 10.1 | — | 0.9 |

0S: -[4GlcAβ1-3GalNAcβ1]-
6S: -[4GlcAβ1-3GalNAc(6S)β1]-
4S: -[4GlcAβ1-3GalNAc(4S)β1]-
SD: -[4GlcA(2S)β1-3GalNAc(6S)β1]-
SB: -[4GlcA(2S)β1-3GalNAc(4S)β1]-
SE: -[4GlcAβ1-3GalNAc(4S,6S)β1]-
(wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (2S), (4S), and (6S) indicate that position 2, 4, or 6 of the monosaccharide residue is sulfated respectively)

Example 2

Preparation of Chondroitin Sulfate Having Decreased Molecular Weight of the Present Invention (2)

Prionace glauca-derived chondroitin sulfate C (weight average molecular weight: 30 kDa, trade name of Seikagaku Corporation: Chondroitin sulfate C, sodium salt (shark cartilage), SG) was used as a starting material and subjected to electron beam irradiation at an irradiation energy of 200 kGy according to the method described in JP-A-2004-43645, whereby a chondroitin sulfate having a decreased molecular weight of the present invention having a weight average molecular weight of 10 kDa and containing a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) in an amount of 73.0% (molar ratio) of the total was obtained as white powder (the detail of the composition of the constituent disaccharide is as shown in Table 2).

TABLE 2

| | Disaccharide composition ratio (%) | | | | | |
|---|---|---|---|---|---|---|
| | 0S | 6S | 4S | SD | SB | SE |
| CSC 10 kDa | 2.9 | 73.0 | 15.3 | 7.8 | — | 1.0 |

0S: -[4GlcAβ1-3GalNAcβ1]-
6S: -[4GlcAβ1-3GalNAc(6S)β1]-
4S: -[4GlcAβ1-3GalNAc(4S)β1]-
SD: -[4GlcA(2S)β1-3GalNAc(6S)β1]-
SB: -[4GlcA(2S)β1-3GalNAc(4S)β1]-
SE: -[4GlcAβ1-3GalNAc(4S,6S)β1]-
(wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (2S), (4S), and (6S) indicate that position 2, 4, or 6 of the monosaccharide residue is sulfated respectively)

Example 3

Effect of Protecting Peritoneum in Peritoneal Dialysis of Chondroitin Sulfate Having Decreased Molecular Weight of the Present Invention (1)

(Experimental Method)

To a Wistar male rat at 8 weeks of age, Midpeliq 250 (trade name, a peritoneal dialysis fluid containing glucose at a concentration of 2.5% (w/v) manufactured by Terumo Corporation) in which a test substance was dissolved at a concentration of 0.1% (w/v) was repetitively administered into the peritoneal cavity once daily at 15 mL/body for 7 days under ether anesthesia. To a control group (Control), Midpeliq 250 was administered in the same manner. On the next day after the final administration, a peritoneal equilibration test was performed, and the peritoneal function was evaluated. To be more specific, Midpeliq 250 was injected into the peritoneal cavity at 60 mL/kg, and 4 hours thereafter, the fluid remaining in the peritoneal cavity was recovered. The amount of the recovered fluid was measured, and the ultrafiltration capacity (water removal rate) of the peritoneum was evaluated.

Incidentally, as the test substance, the following substances were used.

(a) A chondroitin sulfate having a decreased molecular weight of the present invention prepared by electron beam irradiation at an irradiation energy of 300 kGy according to the method of Example 2 and having a weight average molecular weight of 7 kDa (CSC 7 kDa).

(b) A chondroitin sulfate having a decreased molecular weight of the present invention prepared by electron beam irradiation at an irradiation energy of 200 kGy according to the method of Example 2 and having a weight average molecular weight of 10 kDa (CSC 10 kDa).

(c) A chondroitin sulfate having a decreased molecular weight of the present invention prepared by electron beam irradiation at an irradiation energy of 100 kGy according to the method of Example 2 and having a weight average molecular weight of 17 kDa (CSC 17 kDa).

(d) Prionace glauca-derived chondroitin sulfate C (weight average molecular weight: 30 kDa, trade name of Seikagaku Corporation: Chondroitin sulfate C, sodium salt (shark cartilage), SG) used as the starting material (CSC 30 kDa).

(Experimental Results)

The results are shown in FIG. 1. As is apparent from FIG. 1, a statistically significant effect of protecting the peritoneum was observed in the chondroitin sulfates having a decreased molecular weight of the present invention having a weight average molecular weight of 7 kDa, 10 kDa, and 17 kDa as compared with the control group, however, the statistically significant effect was not observed in the shark shoulder cartilage-derived chondroitin sulfate C having a weight average molecular weight of 30 kDa used as the starting material (in the drawing, the expression "Normal" denotes the result in the case where the peritoneal dialysis fluid was not administered). Further, the statistically significant effect was not observed also in a chondroitin sulfate having a decreased molecular weight prepared by using shark fin cartilage-derived chondroitin sulfate C (weight average molecular weight: 20 kDa) as a starting material and hydrolyzing it with hydrochloric acid, having a weight average molecular weight of 10 kDa and containing a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) in an amount of 59.0% (molar ratio) of the total (based on another experiment).

Example 4

Effect of Protecting Peritoneum in Peritoneal Dialysis of Chondroitin Sulfate Having Decreased Molecular Weight of the Present Invention (2)

(Experimental Method)

To a Wistar male rat at 8 weeks of age, Midpeliq 250 (trade name, a peritoneal dialysis fluid containing glucose at a concentration of 2.5% (w/v) manufactured by Terumo Corporation) in which a chondroitin sulfate having a decreased molecular weight of the present invention prepared according to the method of Example 1 and having a weight average molecular weight of 10 kDa (CSC 10 kDa) was dissolved as a test substance at a concentration of 0.1% (w/v) was repetitively administered into the peritoneal cavity once daily at 15 mL/body for 7 days under ether anesthesia. To a control group (Control), Midpeliq 250 was administered in the same manner. On the next day after the final administration, the peritoneum (greater omentum) was excised and the content of lipid peroxide in the tissue was quantitatively determined by a thiobarbituric acid method. An effect of protecting the peritoneum of the test substance was evaluated using an action of inhibiting lipid peroxidation of the peritoneum as an index.

(Experimental Results)

Figure 2:
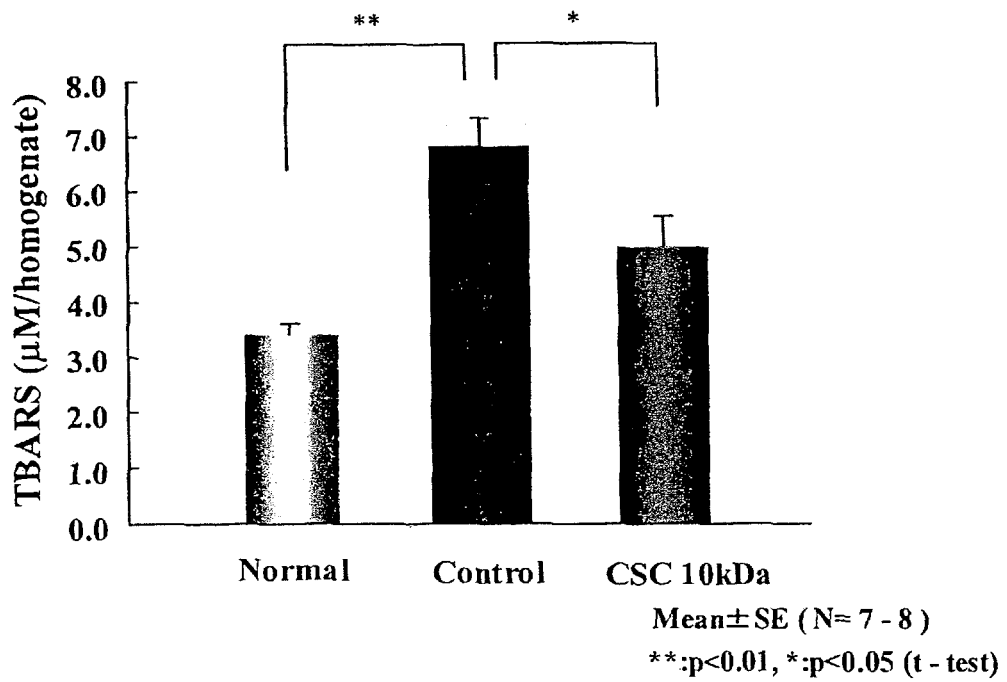
FIG. 2 A graph showing an effect of protecting the peritoneum (action of inhibiting lipid peroxidation of the peritoneum) in peritoneal dialysis of a chondroitin sulfate having a decreased molecular weight of the present invention in Example 4.

The results are shown in FIG. 2. As is apparent from FIG. 2, a statistically significant effect of protecting the peritoneum was observed in the chondroitin sulfate having a decreased molecular weight of the present invention having a weight average molecular weight of 10 kDa as compared with the control group (in the drawing, the expression "Normal" denotes the result in the case where the peritoneal dialysis fluid was not administered).

Example 5

Action of Inhibiting AGE Production of Chondroitin Sulfate Having Decreased Molecular Weight of the Present Invention (Experimental Method)

An experiment was performed according to the method of T. Kiho et al. (Biosci Biotechnol Biochem, 68: 200, 2004). To be more specific, a test substance was dissolved in 0.1 M phosphate buffer (pH 7.4) containing 500 mM glucose and 10 mg/mL bovine serum albumin at a concentration of 0.1% (w/v), and the resulting solution was incubated at 37° C. for 4 weeks. After 4 weeks, a value of fluorescence emitted by AGE was measured at an excitation light wavelength of 355 nm and a measurement wavelength of 460 nm, and the amount of produced AGE was determined, and then, an inhibition rate of AGE production was calculated according to the following calculation equation.

$$\text{Inhibition rate of AGE production}(\%) = [1 - (\text{Fluorescence value when test substance was added}) / (\text{Fluorescence value when test substance was not added})] \times 100 \quad \text{[Equation 1]}$$

(Experimental Results)

The results are shown in Table 3. Incidentally, as the test substance, the following substances were used. Further, as a positive control substance, 1 mM aminoguanidine (a known AGE production inhibitor) was used.

(a) A chondroitin sulfate having a decreased molecular weight of the present invention prepared according to the method of Example 1 and having a weight average molecular weight of 10 kDa (CSC 10 kDa).

(b) A chondroitin sulfate having a decreased molecular weight prepared from whale-derived chondroitin sulfate A (weight average molecular weight: 30 kDa, trade name of Seikagaku Corporation: Chondroitin sulfate A, sodium salt (whale cartilage), SG) by the same method, having a weight average molecular weight of 10 kDa and containing a low proportion (20% to 30%) of a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (CSA 10 kDa).

(c) A chondroitin sulfate having a decreased molecular weight prepared from squid-derived chondroitin sulfate E (weight average molecular weight: 75 kDa, trade name of Seikagaku Corporation: Chondroitin sulfate E, sodium salt (squid cartilage)) by the same method, having a weight average molecular weight of 10 kDa and containing a low proportion (10% to 20%) of a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (CSE 10 kDa).

(d) A dermatan sulfate having a decreased molecular weight prepared by subjecting a cockscomb-derived dermatan sulfate (weight average molecular weight: 40 kDa) to electron beam irradiation at an irradiation energy of 200 kGy according to the method of Example 2, having a weight average molecular weight of 10 kDa and containing a low proportion (10% or less) of a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (DS 10 kDa).

TABLE 3

|  | Concentration | Inhibition rate |
|---|---|---|
| Test substance |  |  |
| CSA 10 kDa | 0.1% (w/v) | 20.7% |
| CSC 10 kDa | Same as above | 54.0% |
| CSE 10 kDa | Same as above | 8.0% |
| DS 10 kDa | Same as above | 7.3% |
| Positive control substance |  |  |
| Aminoguanidine | 1 mM | 52.7% |

As is apparent from Table 3, only the chondroitin sulfate having a decreased molecular weight of the present invention having a weight average molecular weight of 10 kDa (CSC 10 kDa) had an action of inhibiting AGE production comparable to that of aminoguanidine which is a positive control substance.

Example 6

Action of Scavenging Reactive Oxygen of Chondroitin Sulfate Having Decreased Molecular Weight of the Present Invention (Experimental Method)

An experiment was performed according to the method of Olga T. et al. (Toxicological Science, 76: 376, 2003). To be more specific, HL-60 cells differentiated into neutrophil-like cells were suspended in a culture medium at $2 \times 10^6$ cells/mL, and the resulting cell suspension was added to a 96-well plate at 50 μL/well. Then, a test substance was added to the well at 50 μL/well (final concentration: 0.03%, 0.1%, and 0.3% (w/v)). Further, the culture medium was added to the well as a negative control at 50 μL/well. L-012 (final concentration: 100 μM, manufactured by Wako Pure Chemical Industries, Ltd.) which is a fluorescent, substrate for ROS detection and a phorbol ester (phorbol-12-myristate-13-acetate, manufactured by Sigma, final concentration: 5 ng/mL) which is an agent for stimulating ROS production were added to the well at 50 μL/well each, and then, the plate was incubated at 37° C. for 25 minutes in a 5% $CO_2$ incubator. As a background, the plate to which the culture medium was added in place of the phorbol ester was incubated in the same manner. After completion of the incubation, a luminescence intensity (CPS) was measured using a multilabel counter, ARVOSX 1420 (manufactured by PerkinElmer) and an ROS scavenging rate was calculated according to the following calculation equation.

ROS scavenging rate(%)={1−[(CPS in the case of adding test substance)−(CPS in the case of background)]/[(CPS in the case of negative control)−(CPS in the case of background)]}×100   [Equation 2]

(Experimental Results)

The results are shown in Tables 4 and 5. Incidentally, as the test substance, the following substances were used. Further, as a positive control substance, 20 nM staurosporine (a known phorbol ester signal inhibitor) was used.

[Table 4]

(a) A chondroitin sulfate having a decreased molecular weight of the present invention prepared according to the method of Example 1 and having a weight average molecular weight of 1 kDa (CSC 1 kDa).

(b) A chondroitin sulfate having a decreased molecular weight of the present invention prepared according to the method of Example 1 and having a weight average molecular weight of 10 kDa (CSC 10 kDa).

(c) Prionace glauca-derived chondroitin sulfate C (weight average molecular weight: 30 kDa, trade name of Seikagaku Corporation: Chondroitin sulfate C, sodium salt (shark cartilage), SG) used as the starting material (CSC 30 kDa).

(d) A chondroitin having a decreased molecular weight prepared by the same method using chondroitin (weight average molecular weight: 5 kDa, trade name of Seikagaku Corporation: Chondroitin, sodium salt) as a starting material, having a weight average molecular weight of 1 kDa and containing no constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (Ch 1 kDa).

(e) The chondroitin used as the starting material (Ch 5 kDa).

(f) A chondroitin sulfate having a decreased molecular weight prepared by the same method using whale-derived chondroitin sulfate A (weight average molecular weight: 30 kDa, trade name of Seikagaku Corporation: Chondroitin sulfate A, sodium salt (whale cartilage), SG) as a starting material, having a weight average molecular weight of 1 kDa and containing a low proportion (20% to 30%) of a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (CSA 1 kDa).

(g) A chondroitin sulfate having a decreased molecular weight having a weight average molecular weight of 5 kDa and the others are the same as in (f) (CSA 5 kDa).

(h) A chondroitin sulfate having a decreased molecular weight having a weight average molecular weight of 10 kDa and the others are the same as in (f) (CSA 10 kDa).

(i) The whale-derived chondroitin sulfate A used as the starting material (CSA 30 kDa).

(j) A chondroitin sulfate having a decreased molecular weight prepared by the same method using squid-derived chondroitin sulfate E (weight average molecular weight: 75 kDa, trade name of Seikagaku Corporation: Chondroitin sulfate E, sodium salt (squid cartilage)) as a starting material, having a weight average molecular weight of 5 kDa and containing a low proportion (10% to 20%) of a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (CSE 5 kDa).

(k) A chondroitin sulfate having a decreased molecular weight having a weight average molecular weight of 10 kDa and the others are the same as in (j) (CSE 10 kDa).

(l) A chondroitin sulfate having a decreased molecular weight having a weight average molecular weight of 25 kDa and the others are the same as in (j) (CSE 25 kDa).

(m) The squid-derived chondroitin sulfate E used as the starting material (CSE 75 kDa).

(n) A dermatan sulfate having a decreased molecular weight prepared by using a cockscomb-derived dermatan sulfate (weight average molecular weight: 40 kDa) as a starting material and subjecting it to electron beam irradiation at an irradiation energy of 300 kGy according to the method of Example 2, having a weight average molecular weight of 5 kDa and containing a low proportion (10% or less) of a constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (DS 5 kDa).

(o) A dermatan sulfate having a decreased molecular weight prepared by electron beam irradiation at an irradiation energy of 200 kGy and having a weight average molecular weight of 10 kDa and the others are the same as in (n) (DS 10 kDa).

(p) The cockscomb-derived dermatan sulfate used as the starting material (DS 40 kDa).

(q) A cockscomb-derived hyaluronic acid (manufactured by Seikagaku Corporation) having a weight average molecular weight of 900 kDa and containing no constituent disaccharide unit represented by -[4GlcAβ1-3GalNAc(6S)β1]- (wherein GlcA represents a D-glucuronic acid residue; GalNAc represents an N-acetyl-D-galactosamine residue; β1-3 represents a β1-3 glycosidic linkage; β1-4 represents a β1-4 glycosidic linkage; and (6S) indicates that position 6 of the monosaccharide residue is sulfated) (HA 900 kDa).

[Table 5]

(a) A chondroitin sulfate having a decreased molecular weight of the present invention prepared by electron beam irradiation at an irradiation energy of 300 kGy according to the method of Example 2 and having a weight average molecular weight of 7 kDa (CSC 7 kDa).

(b) A chondroitin sulfate having a decreased molecular weight of the present invention prepared by electron beam irradiation at an irradiation energy of 200 kGy according to the method of Example 2 and having a weight average molecular weight of 10 kDa (CSC 10 kDa).

(c) A chondroitin sulfate having a decreased molecular weight of the present invention prepared by electron beam irradiation at an irradiation energy of 100 kGy according to the method of Example 2 and having a weight average molecular weight of 17 kDa (CSC 17 kDa).

TABLE 4

| Test substance | Concentration | ROS scavenging rate |
|---|---|---|
| Ch 1 kDa | 0.1% (w/v) | 11.8% |
| Ch 5 kDa | Same as above | 13.6% |
| CSA 1 kDa | Same as above | 39.7% |
| CSA 5 kDa | Same as above | 41.0% |
| CSA 10 kDa | Same as above | 23.9% |
| CSA 30 kDa | Same as above | 33.4% |
| CSC 1 kDa | Same as above | 72.2% |
| CSC 10 kDa | Same as above | 97.0% |
| CSC 30 kDa | Same as above | 5.0% |
| CSE 5 kDa | Same as above | −9.4% |
| CSE 10 kDa | Same as above | 35.3% |
| CSE 25 kDa | Same as above | 22.4% |
| CSE 75 kDa | Same as above | 21.9% |
| DS 5 kDa | Same as above | 39.4% |
| DS 10 kDa | Same as above | 24.7% |
| DS 40 kDa | Same as above | 11.6% |
| HA 900 kDa | Same as above | 11.5% |
| Positive control substance | | |
| Staurosporine | 20 nM | 97.4% |

TABLE 5

| Test substance | Concentration | ROS scavenging rate |
|---|---|---|
| CSC 7 kDa | 0.03% (w/v) | 57.0% |
| | 0.1% (w/v) | 75.5% |
| | 0.3% (w/v) | 91.5% |
| CSC 10 kDa | 0.03% (w/v) | 54.0% |
| | 0.1% (w/v) | 71.5% |
| | 0.3% (w/v) | 86.5% |
| CSC 17 kDa | 0.03% (w/v) | 34.5% |
| | 0.1% (w/v) | 63.5% |
| | 0.3% (w/v) | 83.5% |
| Positive control substance | | |
| Staurosporine | 20 nM | 98.1% |

As is apparent from Table 4, only the chondroitin sulfates having a decreased molecular weight of the present invention having a weight average molecular weight of 1 kDa and 10 kDa (CSC 1 kDa and CSC 10 kDa) showed excellent ROS scavenging rate, and the ROS scavenging rate for CSC 10 kDa was comparable to that of staurosporine which is a positive control substance. Further, as is apparent from Table 5, the action of scavenging reactive oxygen of the chondroitin sulfate having a decreased molecular weight of the present invention is dependent on its concentration.

Example 7

Effect of Protecting Peritoneum in Peritoneal Dialysis of Chondroitin Sulfate Having Decreased Molecular Weight of the Present Invention (Comparison with Known AGE Production Inhibitors)

(Experimental Method)
To a Wistar male rat at 8 weeks of age, Midpeliq 250 (trade name, a peritoneal dialysis fluid containing glucose at a concentration of 2.5% (w/v) manufactured by Terumo Corporation) in which a test substance was dissolved at a given concentration was repetitively administered into the peritoneal cavity once daily at 15 mL/body for 7 days under ether anesthesia. To a control group (Control), Midpeliq 250 was administered in the same manner. On the next day after the final administration, a peritoneal equilibration test was performed, and the peritoneal function was evaluated. To be more specific, Midpeliq 250 was injected into the peritoneal cavity at 60 mL/kg, and 4 hours thereafter, the fluid remaining in the peritoneal cavity was recovered. The amount of the recovered fluid was measured, and the ultrafiltration capacity (water removal rate) of the peritoneum was evaluated. Further, the concentration of glucose in the recovered fluid was measured, and the peritoneal permeability was evaluated.

Incidentally, as the test substance, the following substances were used.

(a) A chondroitin sulfate having a decreased molecular weight of the present invention prepared by electron beam irradiation at an irradiation energy of 200 kGy according to the method of Example 2 and having a weight average molecular weight of 10 kDa (CSC 10 kDa), concentration: 0.1% (w/v).

(b) Aminoguanidine which is a known AGE production inhibitor, concentration: 0.1% (w/v).

(c) Pyridoxamine which is a known AGE production inhibitor, concentration: 0.05% (w/v).

Figure 3:
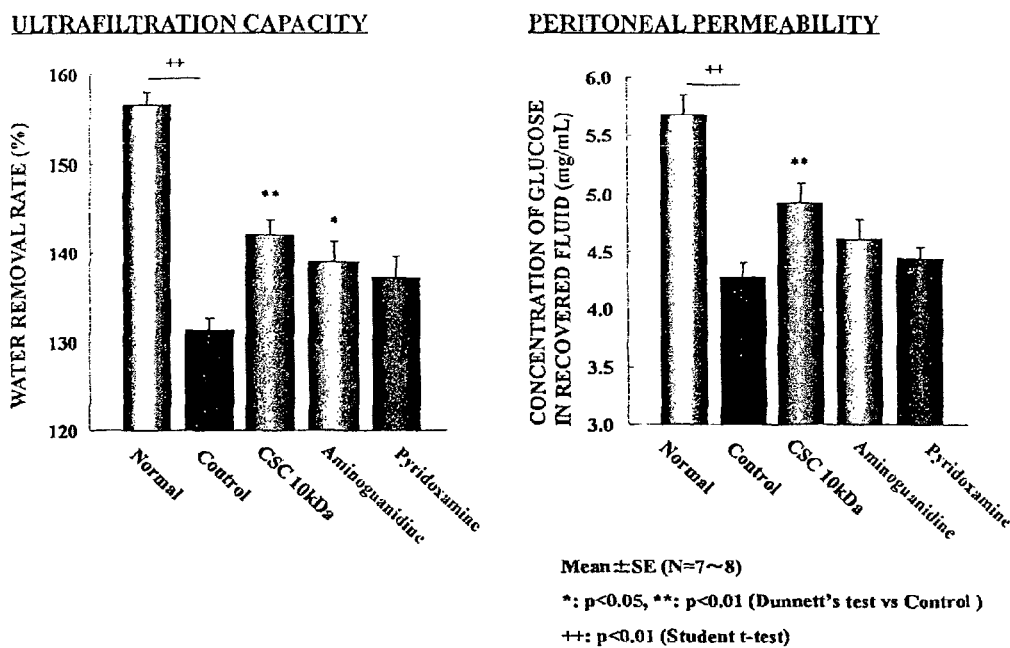
FIG. 3 A graph showing an effect of protecting the peritoneum in peritoneal dialysis of a chondroitin sulfate having a decreased molecular weight of the present invention in Example 7 (comparison with known AGE production inhibitors).

(Experimental Results)
The results are shown in FIG. 3. As is apparent from FIG. 3, a statistically significant effect of protecting the peritoneum was observed in the chondroitin sulfate having a decreased molecular weight of the present invention having a weight average molecular weight of 10 kDa as compared with the control group, and the effect was higher than that of aminoguanidine and pyridoxamine both of which are known AGE production inhibitors (in the drawing, the expression "Normal" denotes the result in the case where the peritoneal dialysis fluid was not administered).

Example 8

Effect of Protecting Peritoneum in Peritoneal Dialysis of Chondroitin Sulfate Having Decreased Molecular Weight of the Present Invention (Comparison with Known Reactive Oxygen Scavengers)

(Experimental Method)
In the same manner as in Example 7, the ultrafiltration capacity (water removal rate) of the peritoneum and the peritoneal permeability were evaluated. Incidentally, as the test substance, the following substances were used.

(a) A chondroitin sulfate having a decreased molecular weight of the present invention prepared by electron beam irradiation at an irradiation energy of 200 kGy according to the method of Example 2 and having a weight average molecular weight of 10 kDa (CSC 10 kDa), concentration: 0.1% (w/v).

(b) L-ascorbic acid which is a known reactive oxygen scavenger, concentration: 0.5 mM.

(d) Trolox which is a known reactive oxygen scavenger, concentration: 0.5 mM.

(d) N-acetyl-L-cysteine which is a known reactive oxygen scavenger, concentration: 10 mM.

Figure 4:
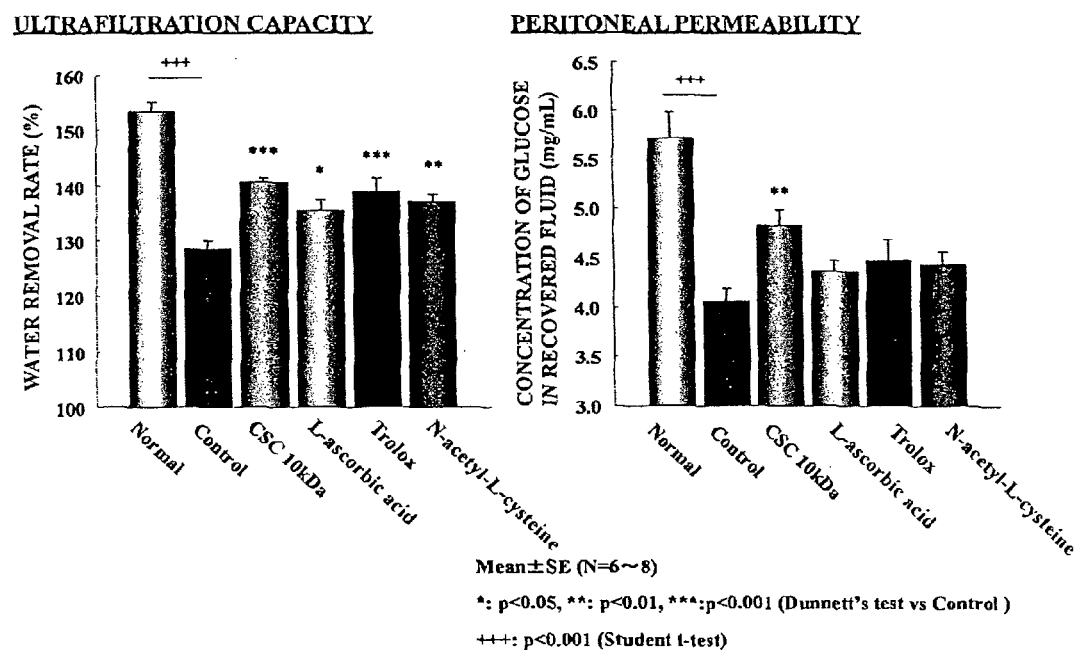
FIG. 4 A graph showing an effect of protecting the peritoneum in peritoneal dialysis of a chondroitin sulfate having a decreased molecular weight of the present invention in Example 8 (comparison with known reactive oxygen scavengers).

(Experimental Results)
The results are shown in FIG. 4. As is apparent from FIG. 4, a statistically significant effect of protecting the peritoneum was observed in the chondroitin sulfate having a decreased molecular weight of the present invention having a weight average molecular weight of 10 kDa as compared with the control group, and the effect was higher than that of known reactive oxygen scavengers (in the drawing, the expression "Normal" denotes the result in the case where the peritoneal dialysis fluid was not administered).

Preparation Example of Peritoneal Dialysis Fluid 1

A peritoneal dialysis fluid having the following composition was prepared according to a common procedure.

| | |
|---|---|
| Glucose | 2.5 (w/v %) |
| Sodium | 135.0 (mEq/L) |
| Magnesium | 1.5 (mEq/L) |
| Calcium | 4.0 (mEq/L) |
| Chlorine | 105.5 (mEq/L) |
| Lactic acid | 35.0 (mEq/L) |
| Chondroitin sulfate having decreased molecular weight of present invention | 0.1 (w/v %) |
| Osmotic pressure ratio (to physiological saline) | about 1.4 to 1.6 |
| pH | 6.3 to 7.3 |

Preparation Example of Peritoneal Dialysis Fluid 2

A peritoneal dialysis fluid having the following composition was prepared according to a common procedure.

| | |
|---|---|
| Chondroitin sulfate having decreased molecular weight of present invention | 2.5 (w/v %) |
| Sodium | 135.0 (mEq/L) |
| Magnesium | 1.5 (mEq/L) |
| Calcium | 4.0 (mEq/L) |
| Chlorine | 105.5 (mEq/L) |
| Lactic acid | 35.0 (mEq/L) |
| Osmotic pressure ratio (to physiological saline) | about 1.4 to 1.6 |
| pH | 6.3 to 7.3 |

INDUSTRIAL APPLICABILITY

The present invention has industrial applicability in that it can provide a chondroitin sulfate having a decreased molecular weight which has utilization as an inhibitor of peritoneal disorder caused by long-term use of a peritoneal dialysis fluid containing glucose or a polysaccharide thereof as an osmotic agent, utilization as an osmotic agent in a peritoneal dialysis fluid, and the like.

The invention claimed is:

1. A method of conducting peritoneal dialysis, comprising the step of:
   administering into the peritoneal cavity of a patient requiring dialysis, a dialysis fluid comprising:
   a chondroitin sulfate having a decreased molecular weight, characterized by having a weight average molecular weight of from 1000 to 20000 Da and containing a constituent disaccharide unit represented by the following structural formula in an amount of from 65% to 100% (molar ratio) of the total of the disaccharide units in the chondroitin sulfate -[4GLcAβ1-3GaLNAc(6S)β1]- wherein GlcA represents a D-glucuronic acid residue; GaLNAc represents an N-acetyl-D-galactosamine residue; β1-3 represents a β1-3 glycosidic linkage; β1-4 represents a β1-4 glycosidic linkage; and (6S) indicates that position 6 of the N-acetyl-D-galactosamine monosaccharide residue is sulfated.

2. The method of claim 1, wherein the dialysis fluid comprises glucose and/or a polysaccharide of glucose as an osmotic agent.

3. The method of claim 1, wherein said chondroitin sulfate is at a concentration of from 0.01% (w/v) to 1% (w/v) in the dialysis fluid.

4. The method of claim 1, wherein the dialysis fluid does not comprise glucose and/or a polysaccharide of glucose, and said chondroitin sulfate is at a concentration of from 1% (w/v) to 10% (w/v) in the dialysis fluid.

* * * * *